US008676317B1

(12) United States Patent
Kroll et al.

(10) Patent No.: US 8,676,317 B1
(45) Date of Patent: Mar. 18, 2014

(54) SYSTEM AND METHOD FOR ESTIMATING DEFIBRILLATION IMPEDANCE BASED ON LOW-VOLTAGE RESISTANCE MEASUREMENTS USING AN IMPLANTABLE MEDICAL DEVICE

(75) Inventors: Mark W. Kroll, Simi Valley, CA (US); Gabriel A. Mouchawar, Valencia, CA (US); J. Christopher Moulder, Encino, CA (US)

(73) Assignee: Pacesetter, Inc., Sylmar, CA (US)

( * ) Notice: Subject to any disclaimer, the term of this patent is extended or adjusted under 35 U.S.C. 154(b) by 1351 days.

(21) Appl. No.: 11/186,741

(22) Filed: Jul. 20, 2005

(51) Int. Cl.
*A61N 1/00* (2006.01)
*G01R 27/00* (2006.01)
*A61B 5/02* (2006.01)

(52) U.S. Cl.
USPC ............. 607/27; 607/4; 607/28; 324/600; 600/547

(58) Field of Classification Search
USPC ............ 607/4, 27–28; 600/547; 324/600
See application file for complete search history.

(56) References Cited

U.S. PATENT DOCUMENTS

| 4,574,810 | A | * | 3/1986 | Lerman | 607/8 |
| 5,201,865 | A | * | 4/1993 | Kuehn | 607/8 |
| 5,549,646 | A | * | 8/1996 | Katz et al. | 607/8 |
| 5,718,720 | A | * | 2/1998 | Prutchi et al. | 607/28 |
| 5,755,742 | A | * | 5/1998 | Schuelke et al. | 607/27 |
| 5,782,884 | A | * | 7/1998 | Stotts et al. | 607/17 |
| 5,891,179 | A | | 4/1999 | Er et al. | 607/27 |
| 5,944,746 | A | * | 8/1999 | Kroll | 607/27 |
| 6,016,445 | A | * | 1/2000 | Baura | 600/547 |
| 6,253,103 | B1 | * | 6/2001 | Baura | 600/547 |
| 6,269,264 | B1 | * | 7/2001 | Weyant et al. | 600/547 |
| 6,317,628 | B1 | * | 11/2001 | Linder et al. | 600/547 |
| 6,317,633 | B1 | | 11/2001 | Jorgenson et al. | 607/28 |
| 6,400,984 | B1 | * | 6/2002 | Medema | 607/8 |
| 6,445,951 | B1 | * | 9/2002 | Mouchawar | 607/28 |
| 6,721,600 | B2 | | 4/2004 | Jorgenson et al. | 607/27 |
| 2002/0120307 | A1 | | 8/2002 | Jorgenson et al. | 607/27 |
| 2002/0123773 | A1 | * | 9/2002 | Molin | 607/27 |
| 2003/0004547 | A1 | | 1/2003 | Owen et al. | 607/5 |
| 2003/0007910 | A1 | | 1/2003 | Diamant Lazarovich et al. | 422/186.18 |
| 2003/0105500 | A1 | * | 6/2003 | Anderson et al. | 607/27 |
| 2003/0120170 | A1 | * | 6/2003 | Zhu et al. | 600/547 |
| 2003/0236468 | A1 | * | 12/2003 | Chapman et al. | 600/547 |
| 2004/0024424 | A1 | * | 2/2004 | Propp et al. | 607/27 |
| 2004/0064161 | A1 | * | 4/2004 | Gunderson et al. | 607/28 |
| 2004/0073266 | A1 | * | 4/2004 | Haefner et al. | 607/27 |
| 2004/0162593 | A1 | | 8/2004 | Jorgenson et al. | 607/27 |
| 2005/0049646 | A1 | * | 3/2005 | Czygan et al. | 607/27 |

FOREIGN PATENT DOCUMENTS

| EP | 0715866 A2 | 6/1996 |
| EP | 0715866 A3 | 6/1996 |
| EP | 0715866 B1 | 6/1996 |
| WO | WO 2004/011090 A2 | 2/2004 |
| WO | WO 2004/011090 A3 | 2/2004 |
| WO | WO 2004/028617 A2 | 4/2004 |
| WO | WO 2004/028617 A3 | 4/2004 |

* cited by examiner

*Primary Examiner* — Nicole F Lavert

(57) ABSTRACT

Techniques are provided for estimating defibrillation impedance of an implantable cardioverter/defibrillator (ICD). Briefly, at least two low-voltage resistance values are measured at different voltages using a pair of stimulation electrodes connected to the ICD. High-voltage defibrillation impedance is then estimated by the ICD based on a weighted combination of the measured resistance values. In one example, a set of weight coefficients, calculated during an initial calibration procedure, are applied to the measured resistance values to produce the estimate of the high-voltage defibrillation impedance. The weight coefficients are updated whenever a defibrillation shock is delivered, based on actual defibrillation impedance values measured during the shock.

13 Claims, 9 Drawing Sheets

SYSTEM AND METHOD FOR ESTIMATING DEFIBRILLATION IMPEDANCE BASED ON LOW-VOLTAGE RESISTANCE MEASUREMENTS USING AN IMPLANTABLE MEDICAL DEVICE

FIELD OF THE INVENTION

The invention generally relates to implantable medical devices for delivering high-voltage shocks to cardiac tissue, such as cardioverter/defibrillators (ICDs), and in particular to techniques for estimating high-voltage impedance for use with such systems.

BACKGROUND OF THE INVENTION

An ICD is an implantable medical device that detects atrial fibrillation (AF) or ventricular fibrillation (VF) within the heart of a patient then delivers one or more high-voltage electrical shocks using a set of leads having electrodes implanted in the heart in an attempt to terminate such fibrillation and revert the heart to a normal sinus rhythm. Fibrillation pertains to the chaotic beating of the chambers of the heart. During fibrillation, there is little or no net blood flow in or out of the fibrillating chambers. AF (i.e. fibrillation occurring within the atrial chambers of the heart) is not typically life-threatening, though it can sometimes trigger VF. VF (i.e. fibrillation occurring within the ventricular chambers of heart) is fatal if not terminated. VF is treated by automatically delivering one or more high-voltage defibrillation shocks directly to the ventricles of the heart using the ICD. State-of-the-art ICDs typically deliver defibrillation shocks at voltages in the range of 100 to 500 volts (V).

It is important to know the impedance of a defibrillation system. Following device implementation, typically, one or more high-voltage test shocks are delivered to the heart of the patient using the ICD and the resulting defibrillation impedance is measured and recorded. A physician examines the impedance values to verify that they are within an acceptable range. Abnormal defibrillation impedance values can indicate, for example, that the leads are defective or were not properly implanted. However, even if the defibrillation impedance values are initially within an acceptable range, defibrillation impedance can change during the months or years following implantation. Shifts in defibrillation impedance can indicate lead movement or lead fracture, fibrosis, or even electrolyte problems within the heart. A significant change in defibrillation impedance can reduce the effectiveness of defibrillation shocks. Lead fracture, indicated by a very high impedance value, typically results in a complete failure to deliver an adequate defibrillation shock.

State-of-the-art ICDs are capable of performing an automatic defibrillation impedance test to verify that impedance remains within acceptable range. Typically, a low-voltage pulse between five and ten volts is periodically delivered to the heart and the resulting impedance is measured to verify that it is within an acceptable range. Low-voltage pulses (i.e. less than 10 volts) are typically employed during the test so as not to cause pain within the patient or to unduly deplete the power supply of the ICD. However, for a variety of reasons, defibrillation impedance measurements based on low-voltage pulses are extremely inaccurate, i.e. the measurements are usually not indicative of the impedance that would actually arise if a high-voltage defibrillation shock were delivered. For example, low-voltages create only low current densities around the electrodes. These low current densities do not recruit very many ionic species and hence have a very high-voltage drop associated therewith. Thus, impedance measurements are non-linear with voltage. Other problems arise because red blood cells are insulators at low frequencies but become conductors at high frequencies. Thus, depending upon the spectral content of the test pulse as compared with the spectral content of the actual high-voltage defibrillation shock, there may be significant impedance measurement errors. As a result, the typical defibrillation impedance detection function provided within an ICD is only capable, at best, of reliably detecting lead fracture and is not typically useful for detecting other variations in defibrillation impedance, which may reduce the effectiveness of subsequent defibrillation shocks.

Accordingly, it would be highly desirable to provide improved techniques for estimating defibrillation impedance using an ICD or other implantable medical device and is to that end that the invention is primarily directed.

SUMMARY

Techniques are provided for estimating the impedance associated with a pair of stimulation electrodes of an implantable medical system. In a method implementation, electrical resistance values associated with, at least, two different voltages are measured using the pair of stimulation electrodes. Then, the impedance associated with the pair of stimulation electrodes at yet another voltage is estimated based on a weighted combination of the measured resistance values. In an embodiment wherein the implantable medical system includes an ICD, the resistance values are preferably measured at relatively low-voltages to avoid patient pain, such as voltages in the range of five to ten volts. The low-voltage resistance values are then used to estimate the impedance associated with a high-voltage defibrillation shock, such as a shock of at least one hundred volts. By using a weighted combination of two or more low-voltage resistance values, a more reliable estimate of high-voltage defibrillation impedance can be achieved than with conventional techniques.

Preferably, the measured resistance values include both direct current (DC)-based resistance values and alternating current (AC)-based resistance values (which may also be referred to as impedance values.) In one specific example, the following low-voltage test pulses are delivered between a right ventricular coil (RVC) electrode and a device housing electrode: a five volt DC pulse; a ten volt DC pulse; and a five volt AC pulse having a frequency of 10 kilohertz (kHz.) By using test pulses having different voltages and different current characteristics, a more reliable estimate of high-voltage defibrillation impedance is achieved by taking into account the nonlinearity of the impedance. In this regard, the resistance measured using the 5 volt DC pulse is typically fairly high; whereas the resistance measured using the 10 volt DC pulse is lower, due to the nonlinearity in the impedance. The resistance/impedance measured using the 5 volt AC pulse is typically lower than the DC resistance values because it allows conduction across a double layer "capacitor" that is generated at an electrode/electrolyte interface when a pulse is delivered to cardiac tissue. Moreover, an AC pulse at 10 kHz capacitive couples with red blood cells.

A weighted combination of the resistance values measured using these pulses is then employed to estimate the defibrillation impedance. If the estimated defibrillation impedance is outside an acceptable range, appropriate warning signals generated. In some implementations, a 15 volt pulse is additionally delivered between the RVC electrode and a super vena cava (SVC) electrode. The addition of the 15 voltage pulse helps improve the estimate of the defibrillation impedance by providing an additional data point. By delivering the fifteen volt pulse between the RVC electrode and the SVC electrode, rather than between the RVC electrode and the device can, pain is avoided.

In a preferred implementation, a resistance value (R) is measured between the pair of stimulation electrodes at each of a plurality of relatively low-voltages ($V_{n=1\ldots N}$) to thereby obtain an equal plurality of measured resistance values ($R_{n=1\ldots N}$) for the pair of electrodes. The defibrillation impedance is then estimated by applying an equal plurality of predetermined weight coefficients ($K_{n=1\ldots N}$) to the plurality of measured resistance values ($R_{n=1\ldots N}$). In one example, this is performed by calculating: $Z_{defib} = K_1 R_1 + K_2 R_2 + \ldots + K_N R_N$. However, other techniques may be used to derive $Z_{defib}$ from $K_{n=1\ldots N}$ and $R_{n=1\ldots N}$. Moreover, the invention is not limited to estimating high-voltage defibrillation impedance, but may be used to estimate other resistance and/or impedance values, including low-voltage values.

A calibration procedure is preferably performed to determine initial values for the plurality of weight coefficients ($K_{n=1\ldots N}$). In one example, a plurality of initial pulses are delivered at each of the relatively low-voltages ($V_{n=1\ldots N}$) while measuring resistance to obtain an equal plurality of initial resistance values ($R_{n=1\ldots N}$). Then, an initial shock is promptly delivered at the higher voltage ($V_{defib}$) while measuring impedance to obtain an initial defibrillation impedance value ($Z_1$). The steps of delivering the plurality of initial pulses and promptly delivering the initial shock are performed X times so as to generate a total of N times X initial resistance values ($R_{n=1\ldots N; x=1\ldots X}$) and X initial impedance values ($Z_{x=1\ldots X}$). Then, initial values for the weight coefficients ($K_{n=1\ldots N}$) are determined by relating the initial resistance values ($R_{n=1\ldots N; x=1\ldots X}$) to the initial impedance values ($Z_{x=1\ldots X}$). In one example, this is performed by solving the following matrix equation for $K_{n=1\ldots N}$:

$$\begin{bmatrix} Z_1 \\ Z_2 \\ \vdots \\ Z_X \end{bmatrix} = \begin{bmatrix} K_1 R_{1,1} + K_2 R_{1,2} + \ldots + K_N R_{1,N} \\ K_1 R_{2,1} + K_2 R_{2,2} + \ldots + K_N R_{2,N} \\ \vdots \\ K_1 R_{X,1} + K_2 R_{X,2} + \ldots + K_N R_{X,N} \end{bmatrix}.$$

An update procedure is preferably performed to update the values for weight coefficients ($K_{n=1\ldots N}$) whenever a defibrillation shock is delivered. In one example, additional pulses are delivered at each of the N relatively low-voltages ($V_{n=1\ldots N}$) just prior to delivery of a defibrillation shock. Resistance values are measured in response to each of the low-voltage pulses so as to obtain N additional resistance values ($R_{n=1\ldots N; X+1}$). The high-voltage impedance is measured in response to the shock to obtain an additional impedance value ($Z_{X+1}$). Then, the values for the weight coefficients ($K_{n=1\ldots N}$) are updated based on the initial resistance values ($R_{n=1\ldots N; x=1\ldots X}$), the initial impedance values ($Z_{x=1\ldots X}$), the N additional resistance values ($R_{n=1\ldots N; X+1}$) and the additional impedance value ($Z_{X+1}$). In one example, this is performed by solving the following matrix equation for $K_{n=1\ldots N}$ using multiple regression techniques:

$$\begin{bmatrix} Z_1 \\ Z_2 \\ \vdots \\ Z_X \\ Z_{X+1} \end{bmatrix} = \begin{bmatrix} K_1 R_{1,1} + K_2 R_{1,2} + \ldots + K_N R_{1,N} \\ K_1 R_{2,1} + K_2 R_{2,2} + \ldots + K_N R_{2,N} \\ \vdots \\ K_1 R_{X,1} + K_2 R_{X,2} + \ldots + K_N R_{X,N} \\ K_1 R_{X+1,1} + K_2 R_{X+1,2} + \ldots + K_N R_{X+1,N} \end{bmatrix}.$$

System implementations of the invention are also provided herein. Preferably, the systems and techniques of the invention are employed with implantable cardiac rhythm management devices providing pacemaking as well as defibrillation functions. Such devices are referred to herein as pacer/ICDs.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Medical System

Figure 1:
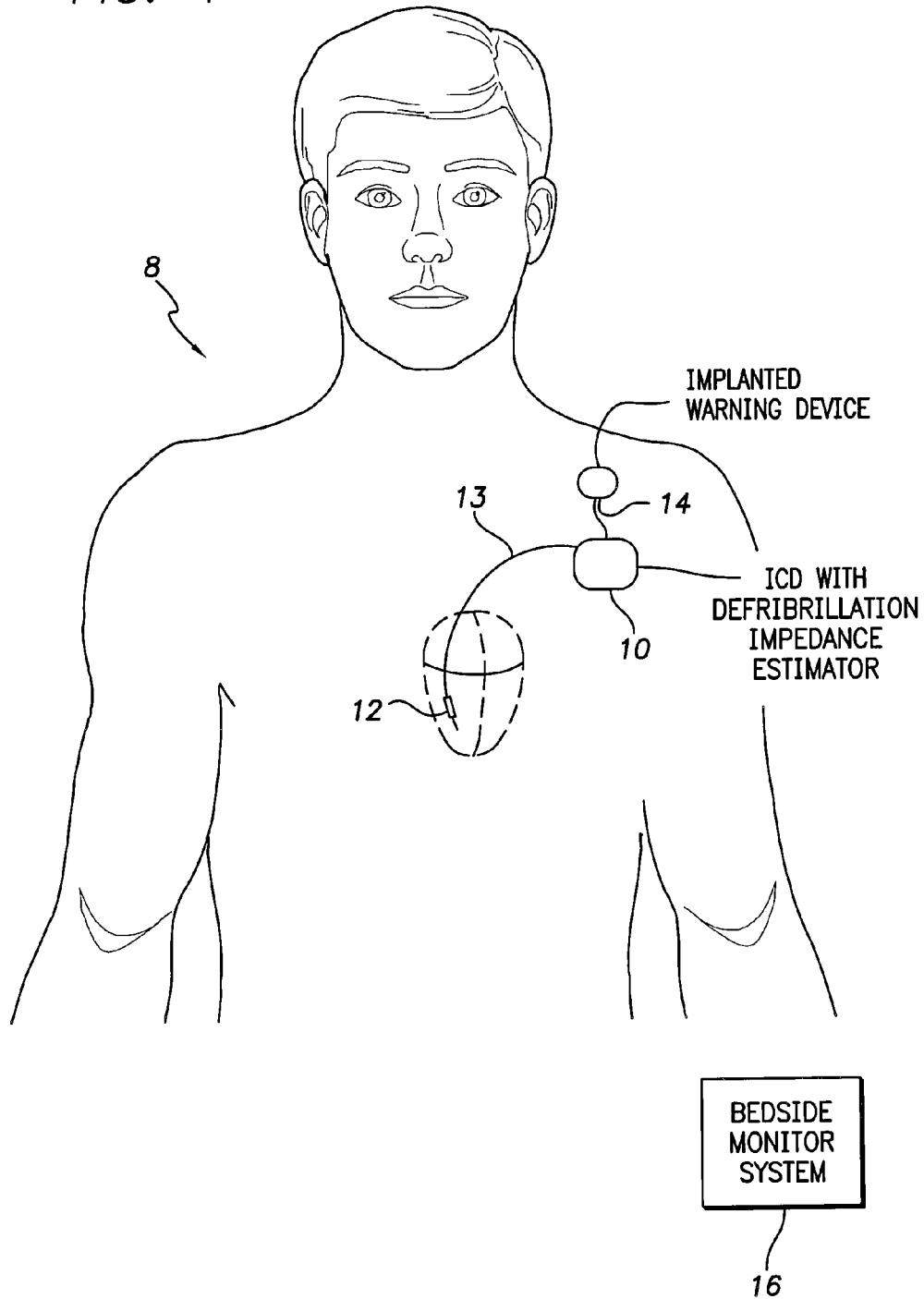
FIG. 1 illustrates pertinent components of an implantable medical system having a pacer/ICD capable of estimating defibrillation impedance based on low-voltage resistance values and for controlling delivery of warning signals if defibrillation impedance is unacceptable.
Figure 8:
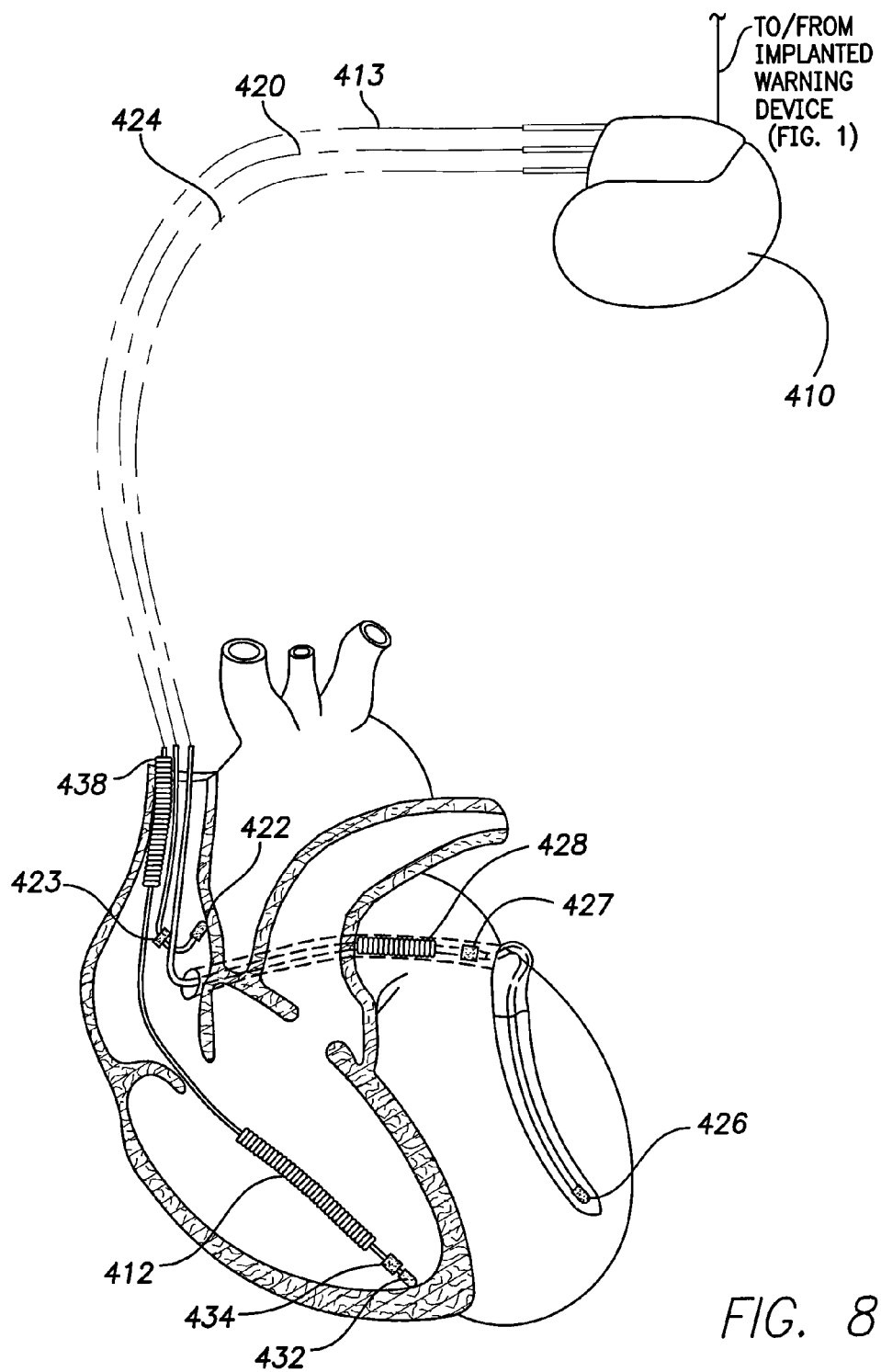
FIG. 8 is a simplified diagram illustrating an exemplary implementation of the pacer/ICD of FIG. 1 equipped to implement the techniques of FIGS. 2-7.

FIG. 1 illustrates an implantable medical system 8 having a pacer/ICD 10 capable of estimating high-voltage impedance based on low-voltage resistance values. To this end, pacer/ICD 10 periodically delivers low-voltage detection pulses to the heart of the patient between a device can electrode (not specifically shown) and a defibrillation coil electrode 12 implanted within the heart of the patient via an RV lead 13. (Typically, additional leads besides the RV lead are implanted as well. A complete set of exemplary leads is shown in FIG. 8.) Resistance values are measured based upon the low-voltage detection pulses. Based on the resistance values and a set of predetermined weight coefficients, the pacer/ICD estimates the impedance that would occur if a high-voltage defibrillation shock were delivered to the patient between the device can electrode and the RVC electrode. This estimation procedure may be performed, for example, once per week to detect any changes in defibrillation impedance that might hinder the pacer/ICD from properly defibrillating the heart.

If the estimated defibrillation impedance is outside an acceptable range, warning signals are generated. For example, the pacer/ICD may activate an internal alarm 14 (or an external bedside monitor 16) to warn the patient. The internal alarm may be a vibrating device or a "tickle" voltage device that, in either case, provides perceptible stimulation to the patient to alert the patient. In one specific example, once the patient perceives the internal stimulation, the patient then uses the bedside monitor to retrieve and display specific, descriptive warning signals from the implanted device. Preferably, the bedside monitor provides both audible and visual descriptions of the detected problem and instructions to consult a physician immediately. Preferably, the bedside monitor is networked with a central server for routing any warning signals directly to the patient's physician or to other appropriate medical professionals. For example, if the bedside monitor is installed within a hospital or clinic, the warning signals may be routed to the appropriate nurse's station. Diagnostic data pertaining to defibrillation impedance may be transmitted from the pacer/ICD to the bedside monitor for further routing to the appropriate medical personnel.

Preferably, upon receipt of the warning, the physician performs otherwise conventional tests to verify that a problem with defibrillation impedance has occurred. Then, the physician adjusts the leads to improve defibrillation impedance or if necessary, replaces one or more of the leads. Since it may take some time before the physician can remedy the lead problem, the implanted system is preferably equipped to automatically switch to a different set of defibrillation electrodes upon detection of an impedance problem. Additionally, or in the alternative, the implanted system may also be equipped to automatically adjust characteristics of a defibrillation shock, such as its voltage or waveform, in an attempt to compensate for the impedance problem. This is useful if the estimated impedance is only slightly outside of an optimal range or if the system includes only a single pair of electrodes suitable for defibrillation (such that switching to a different pair of electrodes is not feasible.)

Thus, FIG. 1 provides an overview of an implantable system for estimating high-voltage defibrillation impedance based on low-voltage resistance values, for delivering warning signals in response thereto, and for taking remedial action. Although a pacer/ICD is illustrated in FIG. 1, it should be understood that the detection techniques of the invention may be implemented within other implantable medical devices such as dedicated defibrillation devices (not capable of providing cardiac pacing therapy) or stimulation devices for stimulating other tissues, such as tissue of the central nervous system. Moreover, techniques of the invention are not limited to estimating only high-voltage impedance values, but may also be used to estimate low- or medium-voltage impedance or resistance values as well. Indeed, techniques of the invention may be exploited to estimate low-voltage impedance based on high-voltage resistance values, in circumstances where warranted. As used herein, "low-voltage" typically refers to voltages no greater than 15 volts; whereas "high-voltage" refers to voltages at or about 100 volts.

As a matter of terminology, "impedance" is typically associated with AC signals; whereas "resistance" is typically associated with DC signals. Since defibrillation shocks are usually biphasic or multiphasic signals, the term "impedance" is generally used herein when referring to defibrillation shocks. Since the low-voltage detection pulses described herein are primarily DC pulses, the term "resistance" is generally used when referring to the low-voltage pulses. However, defibrillation shocks can potentially be DC shocks, and it should be understood that the techniques of the invention may be exploited to estimate the impedance/resistance of shocks that are either DC or AC or some combination thereof. Moreover, the low-voltage detection pulses can potentially have AC components as well. Indeed, one of the detection pulses used in the preferred implementation is a five volt AC pulse having a 10 kHz frequency. Hence, it should also be understood that the techniques of the invention may utilize detection pulses that are either DC or AC or some combination thereof. Accordingly, for the sake of generality the terms "impedance" and "resistance," as used herein, are interchangeable where appropriate.

Insofar as measuring the impedance/resistance associated with a pair of stimulation electrodes is concerned, the measured value encompasses the impedance/resistance of the tissues between the pair of electrodes, as well as the impedance/resistance of the leads and electrical circuitry leading to/from the electrodes. In other words, the pertinent impedance/resistance value to be measured is the "loop" or "complete circuit" impedance/resistance value.

Note also that, whereas internal signal transmission lines for interconnecting the various implanted components are shown in FIG. 1, wireless signal transmission may alternatively be employed. In addition, the particular locations of the implanted components are merely exemplary. Also, it should be appreciated that systems provided in accordance with invention need not include all of the components shown in FIG. 1. In many cases, for example, the implantable system will include only the pacer/ICD and its leads, with any warnings transmitted to the bedside monitor. In other cases, an implantable warning device will be employed but no bedside monitor. These are just a few exemplary embodiments. No attempt is made herein to describe all possible combinations of components that may be provided in accordance with the general principles of the invention.

Defibrillation Estimation Technique

Figure 2:
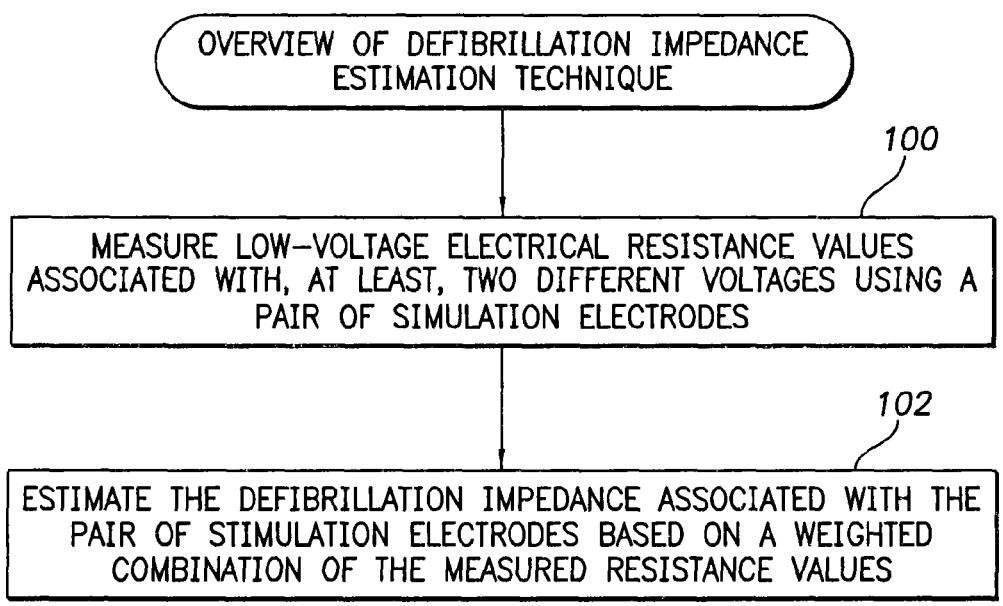
FIG. 2 is a flow chart providing an overview of the method for estimating impedance, which may be performed by the system of FIG. 1 to estimate defibrillation impedance.

FIG. 2 broadly summarizes the estimation technique of the invention. Briefly, at step 100, the pacer/ICD of FIG. 1 (or other implantable medical device) measures low-voltage electrical resistance values associated with, at least, to different voltages using a selected pair of stimulation electrodes, such as the RVC electrode and the device can electrode. Then, at step 102, the pacer/ICD estimates the high-voltage impedance associated with the pair of stimulation electrodes based on a weighted combination of the measured resistance values. By employing a weighted combination of two or more low-voltage resistance values measured at different voltages, the pacer/ICD can render an estimate of the high-voltage impedance that takes into account the nonlinearity of impedance. The different voltages preferably differ from one another by at least five volts to ensure measurable differences in resistance due to nonlinearity. The resistance measurements are preferably made using a series of detection pulses that includes both DC and AC pulses.

By using detection pulses having different current characteristics as well as different voltages, the reliability of the estimation is further improved. In one example, resistance is measured using a 5 volt DC pulse; a 10 volt DC pulse and a 5 volt AC pulse having a frequency of about 10 kHz. As noted above in the Summary, resistance measured using the 5 volt DC pulse is typically fairly high; whereas resistance measured using the 10 volt DC pulse is lower, due to the nonlinearity in the impedance. The resistance/impedance measured using the 5 volt AC pulse is typically lower than the DC resistance values because it allows conduction across the double layer "capacitor" that is generated at the electrode/electrolyte interface when the pulse is delivered to cardiac tissue. Moreover, an AC pulse at 10 kHz capacitive couples with red blood cells and is thereby further influenced by the nonlinearity. Hence, the three different pulses yield different resistance values due to nonlinearity, permitting a weighted combination of the resistance values to be used to estimate defibrillation impedance.

Optionally, resistance is also measured using a 15 volt DC pulse delivered between RVC and SVC. The additional data point derived from the 15 volt pulse helps improve the estimation of defibrillation impedance—even when impedance is being estimated for a different pair of electrodes, such as RVC/can. In particular, the use of the 15 volt pulse helps pick up electrolyte and hematocrit changes. Of course, the extra 15 volt DC pulse is even more beneficial when the pacer/ICD is attempting to estimate RVC/SVC defibrillation impedance.

Turning now to FIGS. 3-6, an exemplary implementation of the estimation technique of the invention will now be described. At step 200 of FIG. 3, the pacer/ICD performs a calibration procedure to determine the initial high-voltage defibrillation impedance associated with a selected pair of electrodes of the pacer/ICD system, as well as to determine initial values for weight coefficients to be used to make subsequent estimations. The calibration procedure, which is described in greater detail below with reference to FIG. 4, involves delivering a series of test defibrillation shocks under the supervision of a physician or other medical professional and automatically measuring and storing corresponding resistance values. Then, beginning at step 202, the pacer/ICD periodically performs an estimation procedure to estimate the current or latest high-voltage defibrillation impedance for the selected pair of electrodes to permit detection of any variations in defibrillation impedance from the initial calibration value. The estimation procedure, which is described in detail with reference to FIG. 5, involves delivering low-voltage pulses and measuring low-voltage resistance values. The weight coefficients determined during calibration procedure are applied to the low-voltage resistance values to estimate the current defibrillation impedance.

At step 204, pacer/ICD then verifies that the estimated defibrillation impedance is within an acceptable, predetermined range. The acceptable range is preferably programmed into the pacer/ICD by the physician following implant of the device and may vary from the system to system depending upon the characteristics of the pacer/ICD and its leads as well as the characteristics of the patient. In one example, an exemplary range of acceptable defibrillation impedance values for the RVC/can electrodes extends from 20 ohms to 100 ohms.

Assuming, initially, that the estimated defibrillation impedance remains within the acceptable range, the pacer/ICD monitors for VF using conventional detection techniques, at step 206. If VF is detected, one or more defibrillation shocks are delivered to the patient, at step 208, in an attempt to revert the heart to a normal sinus rhythm. Assuming the defibrillation shocks are successful, the pacer/ICD additionally performs an update procedure at step 208 to update the weight coefficients originally calculated during the calibration procedure of step 200, so as to improve the accuracy of further estimations. The update procedure is described below with reference to FIG. 6. Processing returns to step 202 for further periodic estimates of defibrillation impedance.

However, if the estimate of the current defibrillation impedance falls outside of the acceptable range, then step 210 is performed wherein the pacer/ICD generates an immediate warning signal indicating that there may be a problem with the pacer/ICD or one of its leads. As noted above, the warning may be delivered directly to the patient via an implantable warning device and/or may be delivered to a bedside monitor for relaying to a physician via a communication network. The urgency of the warning depends upon how significantly the estimated impedance deviates from the acceptable range. If the estimate of the impedance is significantly outside of the acceptable range such that it appears that a lead fracture has occurred, then an extremely urgent warning is relayed indicating that the pacer/ICD system should be examined immediately to determine if a lead fracture has indeed occurred and, if so, to arrange for replacement of the lead. If the estimate of the impedance is only slightly outside of the acceptable range, then a less urgent warning is relayed indicating that the pacer/ICD system should be examined as soon as is feasible. In any case, the warning relayed to the physician preferably also provides diagnostic information, including the original calibration impedance of the pacer/ICD system as well as each of the various estimated impedance values obtained since calibration, including the most recent estimate that triggered the warning, so that the physician can review the trend in defibrillation impedance. A gradual change in impedance may be due to fibrosis; whereas the sudden change may be due to lead fracture or lead displacement.

If the pacer/ICD is equipped with multiple pairs of electrodes through which defibrillation shocks can be delivered then, at step 210, the pacer/ICD preferably automatically switches to a different pair of defibrillation electrodes, particularly if the estimated defibrillation impedance indicates lead fracture of the primary pair of defibrillation electrodes. So, for example, if the estimated defibrillation impedance for the RVC/can electrode pair indicates possible lead fracture, then the pacer/ICD may switch to, for example, the SVC/can electrode pair or perhaps a left atrial coil/can electrode pair. If the pacer/ICD is only equipped with a single pair of electrodes for delivering defibrillation shocks then, at step 210, pacer/ICD preferably automatically adjusts the shape and/or voltage of the defibrillation shock waveform, if it is so equipped, in an attempt to compensate for the change in impedance. Such adjustments are particularly advantageous if the defibrillation impedance has simply drifted out of the acceptable range. In cases where a lead fracture has occurred, adjustment of the shape and/or voltage of the shock waveform will not likely be effective.

Although described with reference to an example involving delivery of defibrillation shocks in response to VF, techniques of the invention may also be exploited to estimate the impedance of cardioversion shocks delivered in response to AF. Indeed, given that cardioversion shocks are typically more painful for the patient than defibrillation shocks (because the patient is often alert when the cardioversion shock is delivered), it is appropriate to closely detect and track changes in cardioversion impedance for the purposes of pain reduction. In this regard, information pertaining to changes in cardioversion impedance may be used to set the cardioversion shock energy to a value sufficient to address AF while also avoiding unnecessary patient pain.

Figure 3:
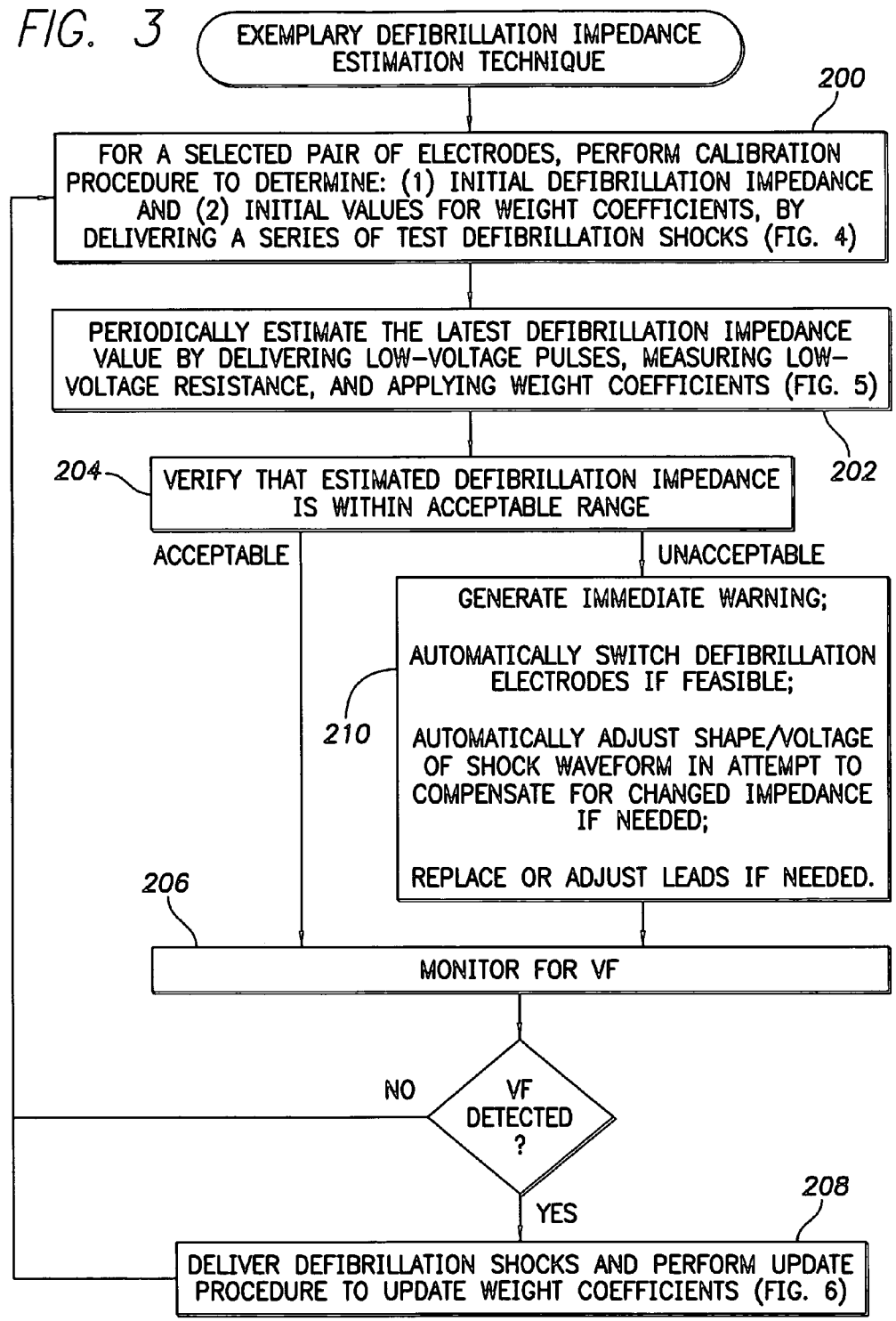
FIG. 3 is a flow chart illustrating an exemplary implementation of the estimation technique of FIG. 2 specifically for use in estimating high-voltage defibrillation impedance for a selected pair of electrodes.
Figure 4:
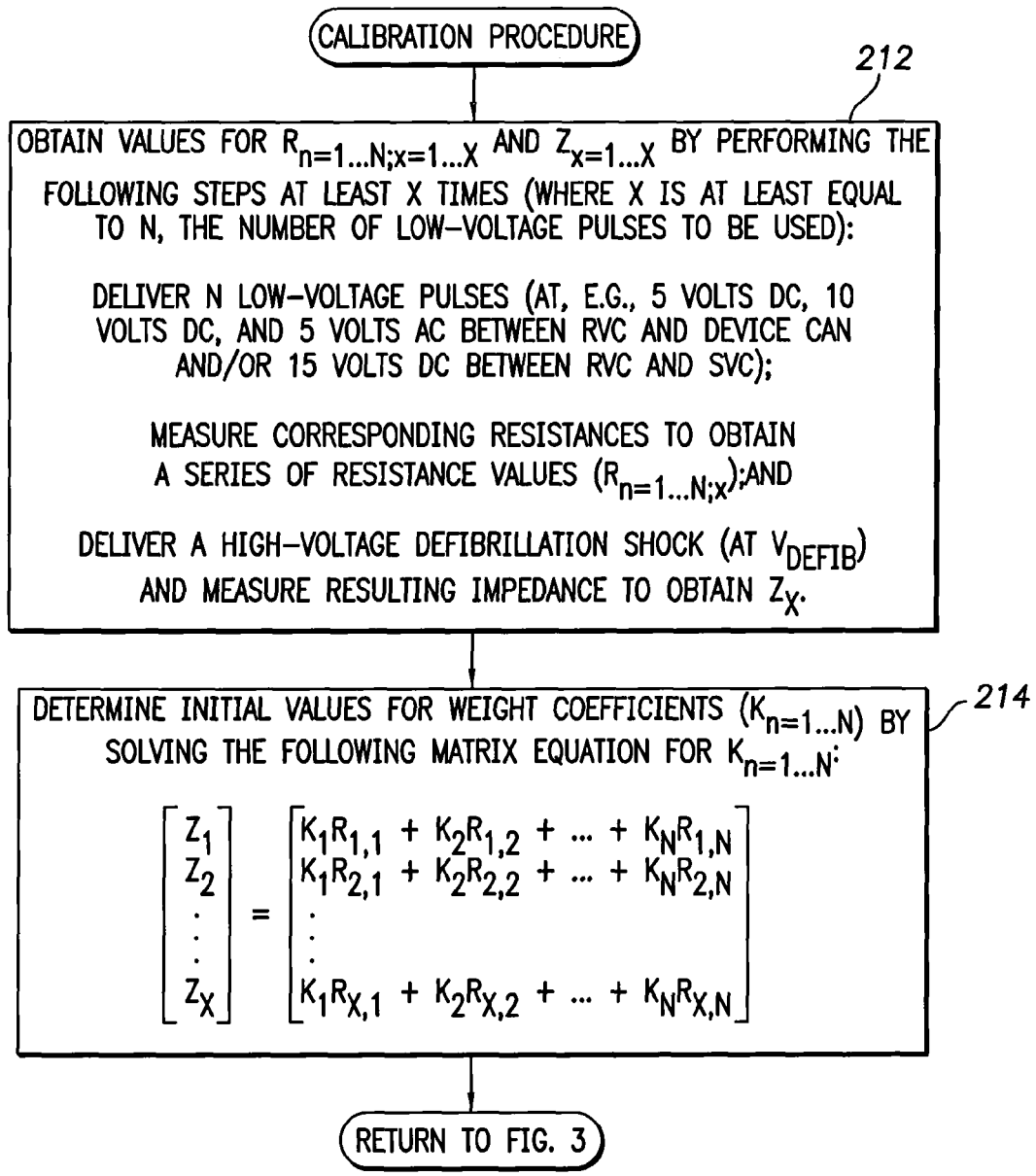
FIG. 4 is a flow chart illustrating an exemplary calibration procedure for use with the implementation of FIG. 3.

FIG. 4 illustrates an exemplary implementation of the calibration procedure of step 200 of FIG. 3. The calibration procedure is preferably performed during a follow-up session following device implementation. During follow-up sessions, the physician ordinarily induces VF under controlled conditions to verify that the pacer/ICD is capable of properly detecting VF and delivering defibrillation shocks sufficient to terminate VF. These test defibrillation shocks are employed by the calibration procedure to determine the initial defibrillation impedance for the pacer/ICD system as well as to calculate an initial set of weight coefficients values for use in subsequent estimations.

More specifically, at step 212, the pacer/ICD obtains a set of resistance and impedance values ($R_{n=1 \ldots N; x=1 \ldots X}$ and $Z_{x=1 \ldots X}$) by performing the following steps at least X times (where X is at least equal to N, the number of low-voltage pulses to be used during each subsequent estimation step):

Deliver N low-voltage pulses using the selected pair of electrodes (at, e.g., 5 volts DC, 10 volts DC, and 5 volts AC);

Measure corresponding resistances to obtain a series of resistance values ($R_{n=1 \ldots N; x}$) for each value of x; and Deliver a high-voltage defibrillation shock (at $V_{defib}$) and measure resulting impedance to obtain a value of $Z_x$ for each value of x.

Then, at step 214, the pacer/ICD calculates initial values for the weight coefficients ($K_{n=1 \ldots N}$) by solving the following matrix equation for $K_{n=1 \ldots N}$ using otherwise conventional techniques:

$$\begin{bmatrix} Z_1 \\ Z_2 \\ \vdots \\ Z_X \end{bmatrix} = \begin{bmatrix} K_1 R_{1,1} + K_2 R_{1,2} + \ldots + K_N R_{1,N} \\ K_1 R_{2,1} + K_2 R_{2,2} + \ldots + K_N R_{2,N} \\ \vdots \\ K_1 R_{X,1} + K_2 R_{X,2} + \ldots + K_N R_{X,N} \end{bmatrix}.$$

For the specific example wherein three low-voltage pulses are to be used to estimate defibrillation impedance (such as the aforementioned 5 volts DC, 10 volts DC, and 5 volts AC pulses), then step 212 is performed to deliver three test defibrillation shocks. Three low-voltage resistance detection of pulses are delivered prior to each of the three test shocks so as to provide a total of nine initial resistance values $R_{n=1 \ldots 3; x=1 \ldots 3}$. The resulting defibrillation impedance is measured for each of the three test shocks so as to provide a total of three initial impedance values $Z_{x=1 \ldots 3}$. Step 214 is then performed to determine initial values for three weight coefficients $K_{n=1 \ldots 3}$ by solving the following matrix equation:

$$\begin{bmatrix} Z_1 \\ Z_2 \\ Z_3 \end{bmatrix} = \begin{bmatrix} K_1 R_{1,1} + K_2 R_{1,2} + K_3 R_{1,3} \\ K_1 R_{2,1} + K_2 R_{2,2} + K_3 R_{2,3} \\ K_1 R_{3,1} + K_2 R_{3,2} + K_3 R_{3,3} \end{bmatrix}.$$

If additionally employing the 15 volt RVC/SVC pulse, an additional test defibrillation shock is employed to generate additional initial impedance value $Z_4$. The additional impedance value and the additional resistance values obtained using the additional 15 volt pulses (i.e. $R_{n=4; x=1 \ldots 4}$) are employed within the above equations. As already noted, even if the estimation technique is intended to estimate defibrillation impedance between the RVC coil and the device can, the additional resistance values obtained using the 15 volt pulse delivered between the RVC and SVC electrodes may be employed as if it were also delivered between the RVC coil and the device can.

In one example, the resistance detection pulses are delivered just prior to charging of the defibrillation capacitors of the pacer/ICD. In another example, the resistance detection pulses are delivered after charging of the capacitors but before delivery of the defibrillation shock. Either technique is effective, so long as the pacer/ICD is consistent, i.e. the pacer/ICD should not combine some resistance values detected based on pulses delivered prior to capacitor charging with other resistance values detected using pulses delivered after capacitor charging.

In some cases, more defibrillation shocks will be delivered during the follow-up session than necessary to calculate the weight coefficients. For example, four or more defibrillation shocks may be delivered even though the estimation technique employs only three resistance detection pulses (and hence only three defibrillation shocks are necessary to calculate the initial values for the weight coefficients.) In that case, preferably, otherwise conventional multiple regression analysis is used to calculate the weight coefficients based on the detected impedance and resistance values. The additional data obtained via the extra defibrillation test shocks helps improve the reliability of the calculation of the initial weight coefficients. Indeed, in some implementations, it may be appropriate to specifically deliver additional defibrillation test shocks to obtain additional data to improve the calculation of the initial weight coefficients. For extremely strong statistical confidence, a general rule of thumb is that there should be ten measurements for each prediction variable to be evaluated. This is typically not practical during the first calibration at the time of implant, as the patient may not tolerate that many test defibrillation shocks. Accordingly, at least initially, the statistical confidence of the predictive variables, i.e. the values for K, is lower than would be preferred in other statistical applications. However, whenever additional shocks are delivered, the statistical confidence in the predictive variables increases.

Also, preferably, the impedance measurements should yield values ranging over the range of values expected for the long term. Thus, high-voltage readings should be taken during inspiration and expiration, systole and diastole, and with SVC on and off. The respiration cycle and cardiac contraction cycle all affect the impedance. Shocks in diastole should be delivered well after the T-wave to avoid the so-called "shock-on-T" induction of VF. The physician may also shift the lead position slightly to vary the impedance. In one implementation, any predictors which are not significant at p=0.01 in the multivariate model are not entered and used until they reach significance with later measurements. All data is preferably saved within the implanted device so that the data can be used later once additional impedance measurements are made that improve statistical significance.

Figure 5:
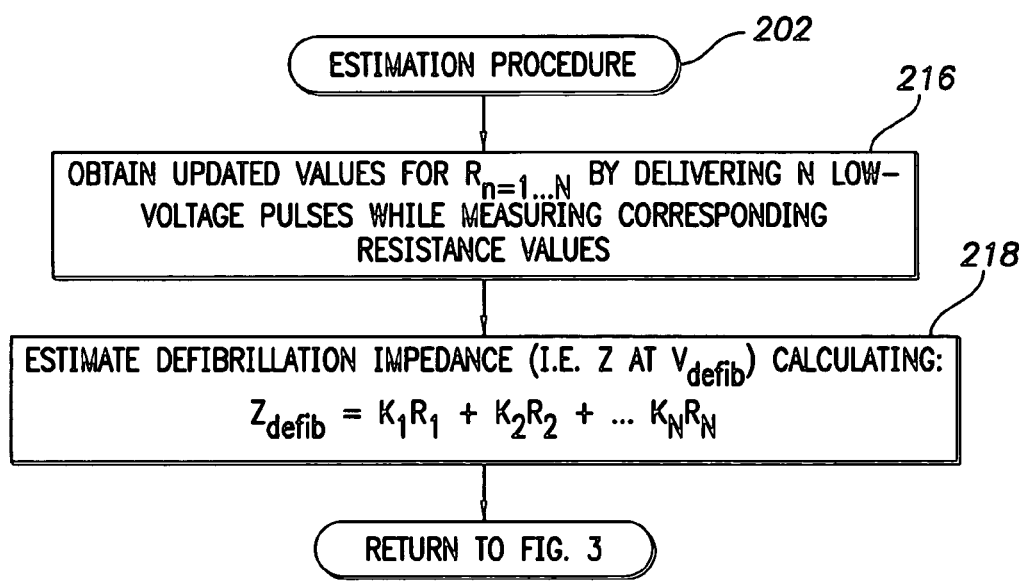
FIG. 5 is a flow chart illustrating an exemplary estimation procedure for use with the implementation of FIG. 3.

FIG. 5 illustrates an exemplary implementation of the estimation procedure of step 202 of FIG. 3. The estimation procedure is preferably performed at least once per day or once per week so as to frequently and periodically obtain a new estimate of defibrillation impedance. The more frequently the estimation is performed, the more quickly the pacer/ICD will be able to detect lead fracture or lead displacement. Preferably, the estimation is performed based upon resistance detection pulses delivered at the same time each day, such as during the night while the patient sleeping, so as to reduce or eliminate any possible variations that might arise due to factors such as patient activity, recently ingested medications, or the like.

At step 216, the pacer/ICD obtains updated values for $R_{n=1 \ldots N}$ by delivering N low-voltage pulses using the selected pair of leads while measuring corresponding resistance values. Then, at step 218, the pacer/ICD estimates the defibrillation impedance (i.e. Z at $V_{defib}$) based on the updated resistance values and the previously calculated weight coefficients by calculating:

$$Z_{defib} = K_1 R_1 + K_2 R_2 + \ldots + K_N R_N.$$

For the example wherein three resistance pulses are used to estimate defibrillation impedance, the pacer/ICD thereby obtains updated values for $R_{n=1\ldots3}$ by delivering three low-voltage pulses. Then, the estimate of the defibrillation impedance is performed by calculating:

$$Z_{defib}=K_1R_1+K_2R_2+K_3R_3.$$

Depending upon the implementation, the pacer/ICD may be programmed to deliver multiple sets of resistance detection pulses during each estimation step so as to calculate multiple estimates for the defibrillation impedance, which are then averaged together to yield a final estimate for comparison against the aforementioned range of acceptable impedance values.

Figure 6:
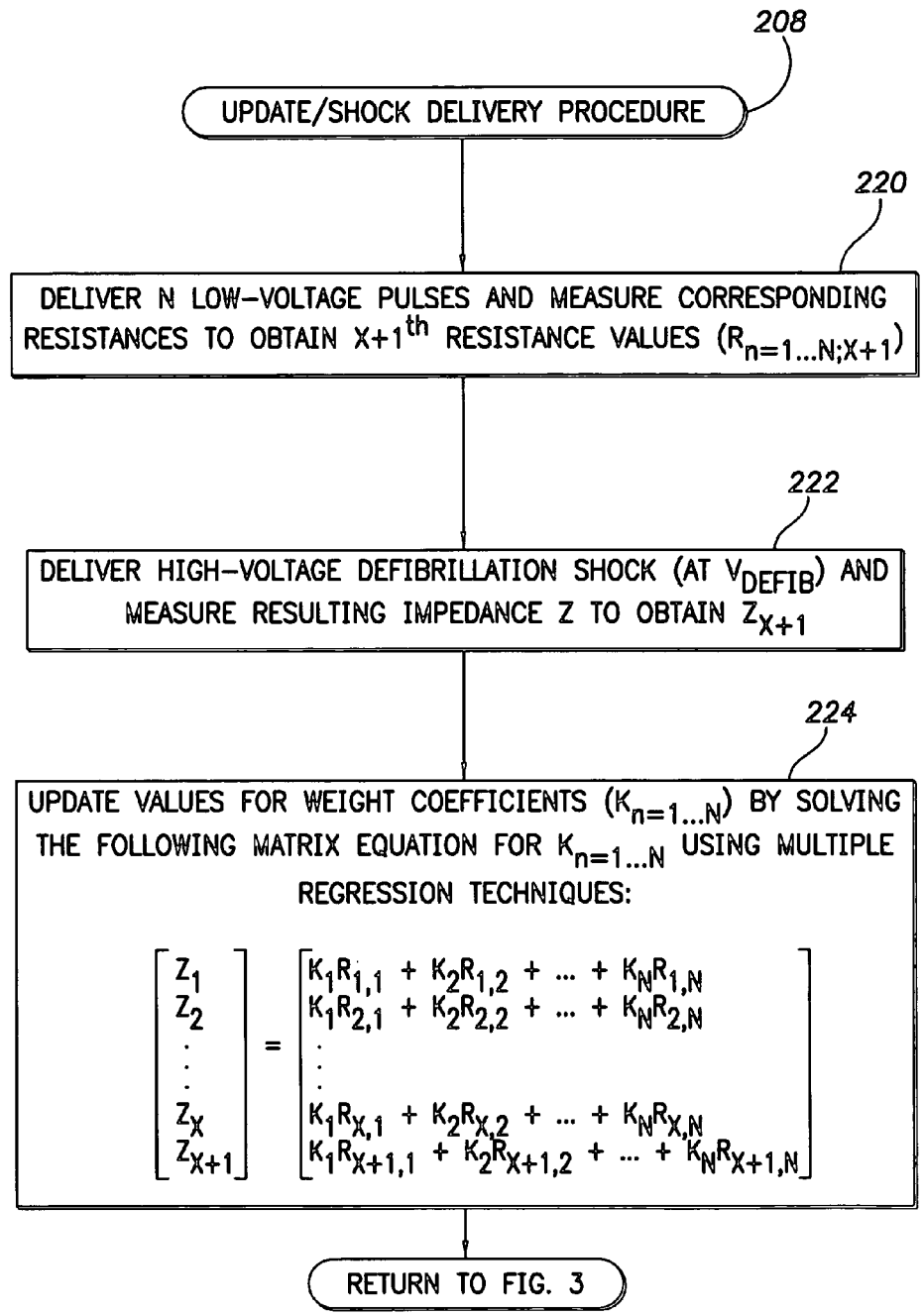
FIG. 6 is a flow chart illustrating an exemplary update/shock delivery procedure for use with the implementation of FIG. 3.

FIG. 6 illustrates an exemplary implementation of the update procedure of step 208 of FIG. 3. As explained, the update procedure is employed to update the values for the weight coefficients whenever a defibrillation shock is actually delivered by the pacer/ICD in response to an episode of VF. At step 220, prior to delivery of the defibrillation shock, the pacer/ICD delivers N low-voltage pulses to the heart of the patient using the selected pair of electrodes and measures corresponding resistances to obtain an additional series of resistance values, herein referred to as the X+1$^{th}$ set of resistance values ($R_{n=1\ldots N; X+1}$). At step 222, the pacer/ICD then delivers a high-voltage defibrillation shock (at $V_{defib}$) and measures the resulting impedance Z to obtain at value for $Z_{x+1}$.

At step 224, the pacer/ICD updates the value of the weight coefficients ($K_{n=1\ldots N}$) by solving the following matrix equation for $K_{n=1\ldots N}$ using multiple regression techniques:

$$\begin{bmatrix} Z_1 \\ Z_2 \\ \vdots \\ Z_X \\ Z_{X+1} \end{bmatrix} = \begin{bmatrix} K_1R_{1,1} + K_2R_{1,2} + \ldots + K_NR_{1,N} \\ K_1R_{2,1} + K_2R_{2,2} + \ldots + K_NR_{2,N} \\ \vdots \\ K_1R_{X,1} + K_2R_{X,2} + \ldots + K_NR_{X,N} \\ K_1R_{X+1,1} + K_2R_{X+1,2} + \ldots + K_NR_{X+1,N} \end{bmatrix}$$

If multiple defibrillation shocks are delivered in response to the episode of VF, then the pacer/ICD will obtain multiple sets of new resistance values and new impedance values (i.e. X+2$^{th}$, X+3$^{th}$, etc. sets of values). Preferably, all of these values are used in the aforementioned equations to update the values of the weight coefficients using multiple regression techniques. Moreover, whenever additional episodes of VF are detected, additional new resistance values and new impedance values are obtained and employed to update the weight coefficients. In other words, the update procedure is not performed only once in response to a single defibrillation shock delivered in response to a single new episode of VF, but is preferably performed whenever additional defibrillation shocks are delivered. The data collected in conjunction with each new defibrillation shock allows the weight coefficients to be refined to improve further estimates of defibrillation impedance.

Although examples have been described herein wherein a linear combination of resistance values is employed to estimate defibrillation impedance, alternative mathematical estimation techniques may potentially be used. In particular, rather than summing weighted resistance values, techniques may be employed wherein a product of weighted resistance values is instead employed. In general, any of a variety of otherwise conventional predictor coupling techniques may potentially be employed, including techniques using polynomial functions as predictors. Those skilled in the art, based on the teachings provided herein, can readily identify suitable alternative estimation techniques that may be employed for use in estimating defibrillation impedance. Otherwise routine experimentation may be employed to verify the reliability of such alternative techniques.

As noted above, the techniques of the invention may be employed to estimate defibrillation impedance for any selected pair of electrodes. For example, separate estimates of defibrillation impedance may be calculated for each of the RVC/can, SVC/can, and the left atrial coil/can electrode pairs. If so, test defibrillation shocks are separately delivered using each of the pairs of electrodes and corresponding impedance and resistance values are measured for use in calculating separate weight coefficients. Thereafter, the defibrillation impedance associated with any of the selected pairs of electrodes can be estimated by delivering resistance detection pulses via those pairs of electrodes in accordance with the techniques are described. One advantage of determining weight coefficients for various pairs of electrodes is that, if a primary pair of electrodes fails, perhaps due to a lead fracture, the pacer/ICD can immediately estimate the defibrillation impedance associated with an alternate pair of electrodes to verify that it is an acceptable range before switching to that alternate pair of electrodes. In this manner, the pacer/ICD can avoid switching to an alternate pair of electrodes that may also be ineffective.

Figure 7:
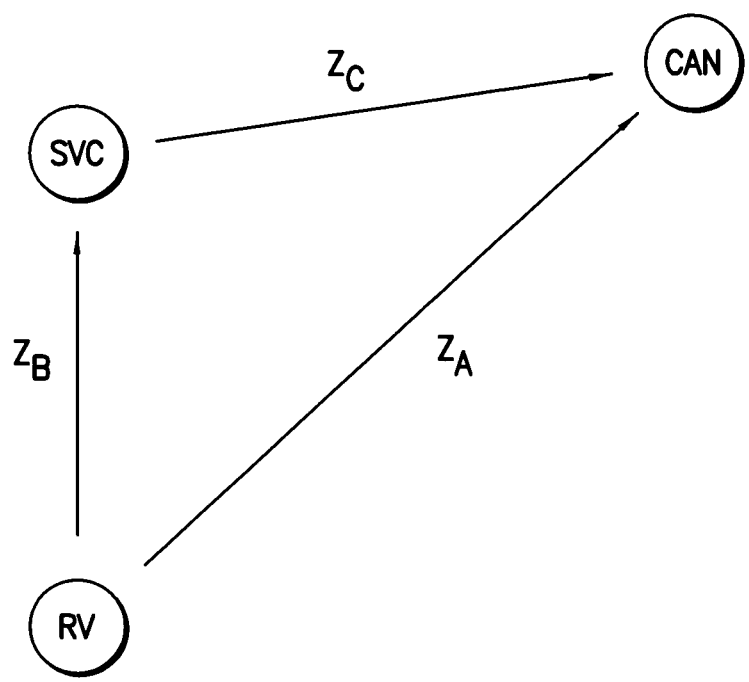
FIG. 7 is a diagram illustrating various impedance vectors for use in estimating defibrillation impedance for alternative pairs of electrodes in accordance with the techniques of FIG. 3.

In some cases, it is desirable to estimate the impedance associated with an individual electrode, rather than associated with an electrode pair. The impedance associated with an individual electrode may be calculated based on the impedance values for pair of electrode so long as at least three electrodes are employed. This is illustrated by way of FIG. 7 for an example utilizing an RV electrode, an SVC electrode, and a device can electrode. First, the techniques described above are employed to separately estimate impedance for each of the following pairs of electrodes: RV/can, RV/SVC and SVC/can. The estimated defibrillation impedance for RV/can pair is identified as $Z_A$; the estimated impedance for the RV/SVC pair identified as $Z_B$; and the estimated impedance for the SVC/can pair is identified as $Z_C$. The individual electrode impedances (i.e. $R_{RV}$, $R_{SVC}$ and $R_{can}$) can then be determined by solving the following equations for $R_{RV}$, $R_{SVC}$ and $R_{can}$:

$$Z_A=R_{RV}+R_{CAN}$$

$$Z_B=R_{RV}+R_{SVC}.$$

$$Z_C=R_{SVC}+R_{CAN}$$

The impedances of other individual electrodes of the lead system can be calculated using similar techniques based on combinations of other electrode pair impedance values. Determination of the individual electrode impedances is helpful in identifying problems in the lead system. Preferably, the individual electrode impedance values are stored as diagnostic data for subsequent review if there appears to be a problem with one or more leads.

What have been described thus far are various techniques for estimating defibrillation impedance for use by a pacer/ICD or other implantable medical device. For the sake of completeness, detailed descriptions of an exemplary pacer/ICD will now be described.

Exemplary Pacer/ICD

Figure 9:
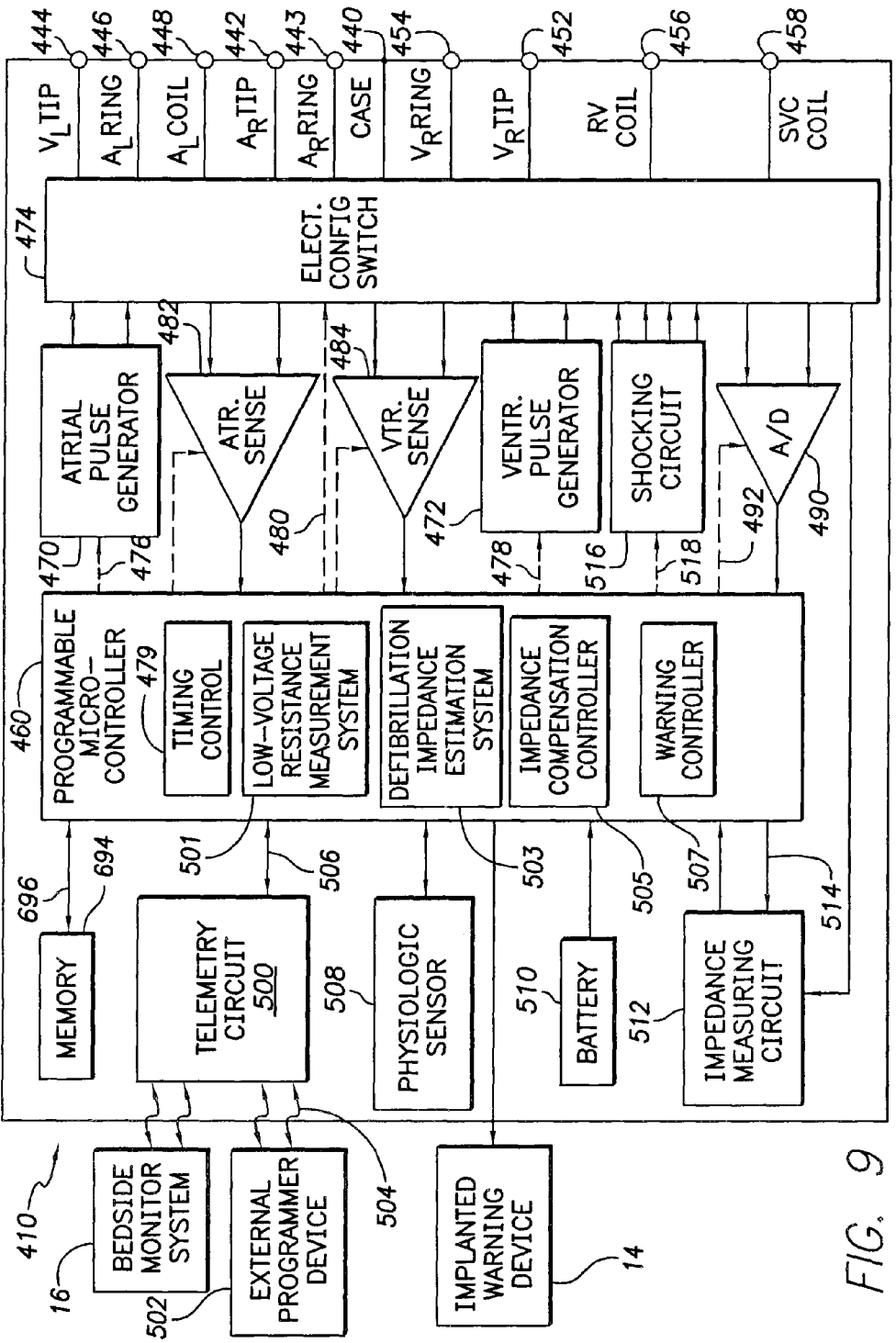
FIG. 9 is a functional block diagram illustrating pertinent internal components of the implantable device of FIG. 8.

With reference to FIGS. 8 and 9, a description of an exemplary pacer/ICD will now be provided. FIG. 8 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart by way of a left atrial lead 420 having an atrial tip electrode 422 and an atrial ring electrode 423 implanted in the atrial appendage. Pacer/ICD 410 is also in electrical communication with the heart by way of a right ventricular lead 413 having, in this embodiment, a right ventricular tip electrode 432, a right ventricular ring electrode 434, a right ventricular (RV) coil electrode 412, and a superior vena cava (SVC) coil electrode 438. Typically, the right ventricular lead 413 is transvenously inserted into the heart to place the RV coil electrode 412 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 8, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A simplified block diagram of internal components of pacer/ICD 410 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 440 for pacer/ICD 410, shown schematically in FIG. 9, is often referred to as the "can", "case" or "case electrode" and may be programmably selected to act as the return electrode for all "unipolar" modes. The housing 440 may further be used as a return electrode alone or in combination with one or more of the coil electrodes, 428, 412 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal (RV COIL) 456, and an SVC shocking terminal (SVC COIL) 458, which are adapted for connection to the right ventricular tip electrode 432, right ventricular ring electrode 434, the $V_R$ coil electrode 12, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 9, an atrial pulse generator 470 and a ventricular pulse generator 472 generate pacing stimulation pulses for delivery by the right atrial lead 420, the right ventricular lead 13, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 used to control the timing of such stimulation pulses (e.g., pacing rate, atrioventricular delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, CS lead 424, and the right ventricular lead 13, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate ventricular tachycardia, high rate ventricular tachycardia, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 13 through the switch 474 to sample cardiac signals across any pair of desired electrodes. The microcontroller 460 is further coupled to a memory 694 by a suitable data/address bus 696, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 694 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 694) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AS-VP delay, AP-VP delay, V-V delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 9. The battery 510 may vary depending on the capabilities of pacer/ICD 410. If the system only provides low-voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 410 is preferably capable of high-voltage therapy and appropriate batteries.

As further shown in FIG. 9, pacer/ICD 410 is shown as having an impedance measuring circuit 512 which is enabled by the microcontroller 460 via a control signal 514. The circuit measures impedance values for use by components of the microcontroller for performing subsequent estimates of defibrillation impedance in accordance with the techniques above. Impedance values may also be used for tracking respiration; for surveillance during the acute and chronic phases for proper lead positioning or dislodgement; for measuring respiration or minute ventilation; for measuring thoracic impedance for use in setting shock thresholds; for detecting when the device has been implanted; and for detecting the opening of heart valves, etc. The impedance measuring circuit 512 is advantageously coupled to the switch 474 so that any desired combination of electrodes may be used.

In the case where pacer/ICD 410 is intended to operate as an implantable cardioverter/defibrillator (pacer/ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 412, and/or the SVC coil electrode 438. The housing 440 may act as an active electrode in combination with the RV coil electrode 412, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with a VS event and/or pertaining to the treatment of tachycardia. Defibrillation shocks are generally of moderate to high energy level (i.e., corresponding to thresholds in the range of 5-40 joules), delivered asynchronously (since VS events may be too disorganized), and pertaining exclusively to the treatment of fibrillation. Accordingly, the microcontroller 460 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a nontracking mode precluding its triggering ventricular outputs in response to sensed atrial events. Numerous other device modes of operation are possible, each represented by standard abbreviations of this type.

Insofar as the defibrillation impedance estimation techniques of the invention are concerned, the microcontroller 460 includes a low-voltage resistance measurement system 501 operative to detect the resistance associated with any selected pair of electrodes by controlling delivery of resistance detection pulses using the techniques discussed above. A defibrillation impedance estimation system 503 estimates the defibrillation impedance associated with the selected pair of electrodes using the measured resistance values in combination with the aforementioned, predetermined weight coefficients. Depending upon the implementation, the impedance estimation system 503 is also operative to estimate the impedance associated with individual electrodes using techniques described above. If a problem with defibrillation impedance is detected, an impedance compensation controller 505 operates to compensate for the problem by, for example, switching to a different pair of defibrillation electrodes or automatically adjusting the voltage/shape of defibrillation shock waveforms to be generated by shocking circuit 516. A defibrillation impedance warning controller 507 controls delivery of warnings pertaining to defibrillation impedance problems by transmitting appropriate control signals to implanted warning device 14 or to bedside monitor system 16 via telemetry circuit 500.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for estimating the defibrillation impedance of a pair of implanted electrodes, said method comprising:

a) performing the following X times, where X is at least equal to N:
delivering a series of N different types of low-voltage pulses between the pair of electrodes;
for each type of low-voltage pulse delivered, measuring the resistance (R) between the pair of electrodes to obtain a resistance value;
delivering a high-voltage defibrillation shock between the electrodes; and
measuring the impedance between the electrodes resulting from the defibrillation shock to obtain an impedance value (Z);

b) determining a plurality of weight coefficients (K), each corresponding to one of the N different types of low-voltage pulses by processing the resistance values and the impedance values;

c) subsequently delivering the series of N different types of low-voltage pulse between the pair of electrodes and measuring corresponding resistances for each type of low-voltage pulse; and d) processing the corresponding resistances and the weight coefficients to obtain the estimated defibrillation impedance for the pair of electrodes.

2. The method of claim 1 wherein the N different types of low-voltage pulses comprises at least one of a DC pulse and one of an AC pulse.

3. The method of claim 1 wherein the N different types of low-voltage pulses comprise a DC pulse at a first voltage and a DC pulse at a second voltage.

4. The method of claim 1 wherein determining a plurality of weight coefficients (K), each corresponding to one of the N different types of low-voltage pulses by processing the resistance values and the impedance values comprises:

solving the following matrix equation for $K_{n=1 \ldots N}$ $$\begin{bmatrix} Z_1 \\ Z_2 \\ \vdots \\ Z_X \end{bmatrix} = \begin{bmatrix} K_1 R_{1,1} + K_2 R_{1,2} + \ldots + K_N R_{1,N} \\ K_1 R_{2,1} + K_2 R_{2,2} + \ldots + K_N R_{2,N} \\ \vdots \\ K_1 R_{X,1} + K_2 R_{X,2} + \ldots + K_N R_{X,N} \end{bmatrix}.$$

5. The method of claim 1 wherein the pair of electrodes comprises a right ventricular coil (RVC) electrode and a device housing electrode.

6. The method of claim 1 wherein the pair of electrodes comprises a right ventricular coil (RVC) electrode and a superior vena cava (SVC) electrode.

7. The method of claim 1 wherein the pair of electrodes comprises a superior vena cava (SVC) electrode and a device housing electrode.

8. The method of claim 1 wherein processing the corresponding resistances (R) and the weight coefficients (K) to obtain the estimated defibrillation impedance for the pair of electrodes comprise:

calculating:

$$Z = K_1 R_1 + K_2 R_2 + \ldots + K_N R_N.$$

9. The method of claim 1 further comprising periodically repeating a) and b) to obtain updated coefficient values.

10. The method of claim 1 further comprising repeating a) and b) to obtain updated coefficient whenever a defibrillation shock is delivered.

11. The method of claim 1 wherein:
delivering a defibrillation pulse comprises charging a capacitor; and the series of N different types of low-voltage pulses are delivered prior to charging of the capacitor.

12. The method of claim 1 wherein:
delivering a defibrillation pulse comprises charging a capacitor; and
the series of N different types of low-voltage pulses are delivered after charging of the capacitor but prior to delivery of the defibrillation shock.

13. A system for estimating the defibrillation impedance of a pair of implanted electrodes, said system comprising:
a measurement system operative to performing the following X times, where X is at least equal to N:
deliver a series of N different types of low-voltage pulses between the pair of electrodes;
for each type of low-voltage pulse delivered, measure the resistance (R) between the pair of electrodes to obtain a resistance value;
deliver a high-voltage defibrillation shock between the electrodes; and
measure the impedance between the electrodes resulting from the defibrillation shock to obtain an impedance value (Z);
determine a plurality of weight coefficients (K), each corresponding to one of the N different types of low-voltage pulses by processing the resistance values and the impedance values;
a defibrillation impedance estimation system operative to:
subsequently deliver the series of N different types of low-voltage pulse between the pair of electrodes and measure corresponding resistances for each of the low-voltage pulses; and
process the corresponding resistances and the weight coefficients to obtain the estimated defibrillation impedance for the pair of electrodes.

\* \* \* \* \*